United States Patent
Borg et al.

(10) Patent No.: US 7,815,801 B2
(45) Date of Patent: Oct. 19, 2010

(54) REMOVAL OF SELENIUM IN CONTAMINATED WASTEWATER STREAMS

(75) Inventors: Charles Borg, San Francisco, CA (US); David Friese, Orinda, CA (US); Tyze-Kuan Tim Yin, Walnut Creek, CA (US)

(73) Assignee: APT Water, Inc., Pleasant Hill, CA (US)

(*) Notice: Subject to any disclaimer, the term of this patent is extended or adjusted under 35 U.S.C. 154(b) by 18 days.

(21) Appl. No.: 12/328,593

(22) Filed: Dec. 4, 2008

(65) Prior Publication Data

US 2009/0152194 A1 Jun. 18, 2009

Related U.S. Application Data

(60) Provisional application No. 61/008,028, filed on Dec. 17, 2007.

(51) Int. Cl.
*C02F 3/00* (2006.01)
(52) U.S. Cl. .................................. 210/610
(58) Field of Classification Search .............. 210/610
See application file for complete search history.

(56) References Cited

U.S. PATENT DOCUMENTS

| | | | |
|---|---|---|---|
| 4,285,765 A * | 8/1981 | Pera et al. | 162/161 |
| 4,915,928 A | 4/1990 | Marcantonio | |
| 5,858,766 A * | 1/1999 | Premuzic et al. | 435/262.5 |
| 5,993,667 A | 11/1999 | Overman | |
| 6,156,191 A | 12/2000 | Overman | |
| 6,183,644 B1 * | 2/2001 | Adams et al. | 210/611 |
| 6,387,262 B1 | 5/2002 | Rittmann et al. | |
| 6,541,240 B1 * | 4/2003 | Kilbane et al. | 435/253.3 |
| 7,140,495 B2 | 11/2006 | Hester et al. | |
| 7,169,295 B2 | 1/2007 | Husain et al. | |
| 7,175,763 B2 | 2/2007 | Husain et al. | |
| 7,186,340 B1 * | 3/2007 | Rittmann et al. | 210/604 |
| 2005/0079114 A1 * | 4/2005 | Dubrovsky | 423/1 |
| 2006/0037896 A1 | 2/2006 | Cote et al. | |
| 2008/0302720 A1 * | 12/2008 | Bowman | 210/601 |

FOREIGN PATENT DOCUMENTS

| | | |
|---|---|---|
| WO | WO 87/00161 A1 | 1/1987 |
| WO | WO 92/07798 A1 | 5/1992 |
| WO | WO 94/22773 A1 | 10/1994 |

OTHER PUBLICATIONS

Bem, E. M., "Determination of Selenium in the Environment and in Biological Material", *Environmental Health Perspectives*, 37:183-200 (1981).

(Continued)

*Primary Examiner*—Chester T Barry
(74) *Attorney, Agent, or Firm*—Judy M. Mohr; LeeAnn Gorthey; King & Spalding LLP (57) ABSTRACT

Compositions and methods for the removal of selenium species from water containing high-salt concentrations and/or petroleum contaminants are described. The compositions and methods use a selenium-reducing microorganism adapted to adverse environments.

29 Claims, 2 Drawing Sheets

OTHER PUBLICATIONS

Campbell, A.D., "Critical Evaluation of Analytical Methods for the Determination of Trace Elements in Various Matrices: Part 1: Determination of Selenium in Biological Materials and Water", 56(5):645-651 (1984).

The International Search Report and Written Opinion for PCT application PCT/US2008/013360, Search report dated Jul. 20, 2009, 16 pages (2009).

Chung, J. et al., "Simultaneous bio-reduction of nitrate, perchlorate, selenate, chromate, arsenate, and dibromochloropropane using a hydrogen-based membrane biofilm reactor", *Biodegradation*, 18:199-209 (2007).

Chung, J. et al., "Bioreduction of Selenate Using a Hydrogen-Based Membrane Biofilm Reactor", *Environ. Sci. Technol.*, 30:1664-1671 (2006).

Chung, J. et al., "Bio-reduction of Soluble Chromate using a Hydrogen-Based Membrane Biofilm Reactor", *Water Research*, 40:1634-1642 (2006).

Chung, J. et al., "Bioreduction of Trichloroethene Using a Hydrogen-Based Membrane Biofilm Reactor", *Environ. Sci. Technol.*, 42:477-483 (2008).

Presser, T.S., United States Geological Survey, "Selenium Contamination Associated with Irrigated Agriculture in the Western United States", National Research Program,, Water Resources Division, 7 pages (2007).

Siddique, T. et al., "Bacterial diversity in selenium reduction of agricultural drainage water amended with rice straw", *J. Environ. Qual.*, 34(1):217-226 (2005).

* cited by examiner

REMOVAL OF SELENIUM IN CONTAMINATED WASTEWATER STREAMS

PRIORITY

The present application claims priority to U.S. Provisional Application Ser. No. 61/008,028 filed 17 Dec. 2007. which is hereby incorporated by reference.

TECHNICAL FIELD

The present compositions and methods relate to the removal of selenium species from water containing high-salt concentrations, such as brine water, and/or petroleum contaminants, using a selenium-reducing microorganism.

BACKGROUND

Selenium Properties and Toxicity

Selenium (element Se) is a metalloid that can form organic and inorganic compounds and exist in a number of oxidation states (i.e., II-, 0, II, IV, and VI; although Se[II] is not found in nature). Common selenium containing molecules (and their oxidation states) are Selenium (Se°), selenite (Se[IV], $SeO_3^{2-}$), selenate (Se[VI], $SeO_4^{2-}$), and hydrogen selenide (Se[II-], $H_2Se$).

Selenium is used in the production of meals, glass, pigments, textiles rubber, metal alloys, textiles, petroleum products, photoelectric applications, etc. Selenium was used in pesticides, although use has been curtailed. The toxicity of selenium to mammals and birds is well known. Selenium is required as a trace element in mammals but is toxic in elevated doses, Selenium contamination is ubiquitous in many parts of the world, including the western United States.

Selenium is sufficiently similar in bonding characteristics and size to substitute for sulphur in various metabolic reactions. When incorporated into bacterial sulpher metabolism, selenium can become bonded to carbon and incorporated into selenoamine, a biologically active amino acid. Selenoamine is incorporated into selenoproteins, This selenium can reappear in many "sulpher"-containing biological molecules, including selenocysteine and selenomethionine, which are toxic analogs of cysteine and methionine, respectively. Dimethyl selenide (DMSe, $(CH_3)_2Se$) and dimethyl diselenide (DMDSe, $(CH_3)_2Se_2$) are volatile forms of selenium also believed to be the result of microorganism metabolism.

Oxidized forms of selenium exist as soluble oxyanions in water. Selenate is predominant in freshwater and selenite is predominant in seawater. Neither of these anions reacts appreciably with calcium or magnesium to form a precipitate. Elemental selenium is found in amorphous form (crimson red) or in one of several crystalline forms, which are less colorful. Reduced selenium species include hydrogen selenide ($H_2Se$), methylselenides, and others.

Crude oils often contain high levels of selenium, particularly when associated with geological formations containing marine shales. During refinement, selenium becomes concentrated in refinery effluents in the forms of selenide, selenite, selenate and selenocyanate. The presence of hydrocarbons and other petroleum products complicates selenium removal.

Removal of Selenium from Water

Conventional methods for removing selenium contaminants from water include chemical addition followed by precipitation or adsorption to a solid phase or membrane filtration to separate the oxidized or reduced selenium species. For example, U.S. Pat. No. 4,915,928 describes a process for removing selenium from wastewater using a strong ion exchange resin. U.S. Pat. Nos. 5,993,667 and 6,156,191 described a process for removing selenium from wastewater involving oxidizing seleniumcyanate ions to selenite ions, which are removed by adsorption to ferric hydroxide and other insoluble precipitates. WO 92/07798 describes a method for removing selenium from an aqueous stream using a particular chemical oxidizing agent. U.S. Pub. No. 2005/0079114 describes a method for removing selenium from an aqueous stream using a quaternary ammonium compounds. Generally, zeolites, dithiocarbamates (and polymers, thereof, metal salts (e.g., ferric chloride and ferric sulfate) adsorb selenium is in the form of selenite anions but are not effective in removing selenocyanate ion ($SeCN^-$), which predominate in refinery wastewater and stripped sour water.

Air, ozone, hydrogen peroxide, and chlorine dioxide have been used as oxidizing agents, however, air is ineffective in oxidizing selenocyanate, ozone and hydrogen peroxide conventionally require highly alkaline conditions for maximum effectiveness, and chlorine dioxide is unstable and introduces chloride to the water. While the reduction of selenate (VI) to selenite (IV) is thermodynamically favorable it requires a strong reductant to speed the reaction. Notably, some bacteria are able to reduce selenium metabolically using hydrogen or another reducing gas, which avoids the need for a strong reductant.

Conventional methods for removing selenium from wastewater are not particularly effective in water with high total dissolved solids (TDS), particularly salts. These waters include brine water, which may have well over 1,000 parts per million (ppm) salt.

The need exists for an economical and efficient water treatment process that can remove selenium species from high salt/high TDS water and refinery wastewater.

SUMMARY

The following aspects and embodiments thereof described and illustrated below are meant to be exemplary and illustrative, not limiting in scope.

In some aspects, a method for removing selenium species from high-salt waters is provided, comprising
  contacting high-salt water with at least one selenium reducing bacteria capable of growing in high-salt water in the presence of dissolved hydrogen and an organic carbon source, said contacting forming a reduced selenium species, and
  separating the water from the reduced selenium species.
In some embodiments, the bacteria is selected by:
  (a) growing a naturally-occurring selenium-reducing bacteria under low salt conditions,
  (b) iteratively increasing the salt concentration while maintaining a biofilm comprised of the bacteria, and
  (c) recovering the selenium-reducing bacteria that grow under high-salt conditions.

In some embodiments, selenium reduction is monitored at (b) to ensure the bacteria continue to reduce selenium species. In some embodiments, selenium reduction is monitored at (c) to ensure the bacteria continue to reduce selenium species.

In some embodiments, the bacteria in (a) are selected from the phyla Proteobacteria, Actinobacteria, and Firmicutes.

In some embodiments, the bacteria reduce selenate. In some embodiments, the bacteria reduce selenite.

In some embodiments, the at least one selenium reducing bacteria is a plurality of different selenium reducing bacteria.

In some embodiments, the plurality of bacteria reduce selenate and selenite to Se°.

In some embodiments, the dissolved hydrogen is from hydrogen gas sparged into the water.

In some embodiments, the method is performed in a bioreactor comprising a plurality of hollow filaments, wherein the bacteria form a biofilm on an exterior surface of the hollow filaments and hydrogen gas is introduced to an interior lumen of the hollow filaments.

In particular embodiments, the filaments are comprised of polyester, including e.g., recycled polyester.

In another aspect, a method for selecting a selenium-reducing, high-salt-tolerant microorganism is provided, comprising:
  (a) growing a naturally-occurring selenium-reducing bacteria under low salt conditions,
  (b) iteratively increasing the salt concentration while maintaining a biofilm, and
  (c) recovering the selenium-reducing bacteria that grow under high-salt conditions.

In some embodiments, selenium reduction is monitored at (b) to ensure the bacteria continue to reduce selenium species. In some embodiments, selenium reduction is monitored at (c) to ensure the bacteria continue to reduce selenium species.

In some embodiments, the bacteria in (a) are selected from the phyla Proteobacteria, Actinobacteria, and Firmicutes.

In some embodiments, the bacteria reduce selenate. In some embodiments, the bacteria reduce selenite.

In some embodiments, the naturally-occurring selenium-reducing bacteria is a plurality different selenium reducing bacteria.

In some embodiments, the bacteria reduce selenate and selenite to Se°.

In some embodiments, the dissolved hydrogen is from hydrogen gas sparged into the water.

In some embodiments, the selecting is performed in a bioreactor comprising a plurality of hollow filaments, wherein the bacteria form a film on the outside of the filaments and hydrogen gas is introduced inside the hollow filaments.

In particular embodiments, the filaments are comprised of polyester, including e.g., recycled polyester.

In another aspect, selenium-reducing, high-salt-tolerant bacteria produced as described are provided. In some embodiments, the bacteria are a mixture of different, selenium-reducing, high-salt bacteria.

In another aspect, a business method is provided, comprising.
  obtaining high-salt wastewater from a customer,
  removing selenium from the water using selenium-reducing, high-salt tolerant bacteria,
  returning high-salt, selenium-depleted water to the customer for reuse, and
  charging the customer a price.

In some embodiments, the price for said removing and returning is less than the cost of untreated, essentially selenium-free water.

In a related aspect, a business method is provided, comprising:
  obtaining high-salt wastewater from a customer,
  removing selenium from the water using selenium-reducing, high-salt tolerant bacteria,
  desalinating the water,
  returning low-salt, selenium-depleted water to the customer, and
  charging the customer a price for said removing, desalinating, and returning that is less than the cost of untreated, essentially selenium-free water.

In some embodiments, the step of removing selenium is performed in a bioreactor comprised of hollow filaments for supporting a biofilm comprised of the bacteria, In some embodiments, the selenium-reducing, high-salt tolerant bacteria are obtained by
  (a) growing a naturally-occurring selenium-reducing bacteria under low salt conditions,
  (b) iteratively increasing the salt concentration to, and
  (c) recovering the selenium-reducing bacteria that grow under high-salt conditions.

In some embodiments, removing selenium from the water is performed at a worksite.

In another aspect, a method for removing selenium species from petroleum-contaminated water is provided, comprising
  contacting petroleum-contaminated water with at least one selenium reducing bacteria capable of growing in petroleum-contaminated water in the presence of dissolved hydrogen and an organic carbon source, said contacting forming a reduced selenium species, and
  separating the water from the reduced selenium species.

In some embodiments, the bacteria is selected by:
  (a) growing a naturally-occurring selenium-reducing bacteria under conditions of low petroleum-contamination,
  (b) iteratively increasing the concentration of at least one petroleum-contaminant while maintaining a biofilm comprised of the bacteria, and
  (c) recovering the selenium-reducing bacteria that grow in petroleum-contaminated conditions.

In some embodiments, selenium reduction is monitored at (b) to ensure the bacteria continue to reduce selenium species. In some embodiments, selenium reduction is monitored at (c) to ensure the bacteria continue to reduce selenium species.

In some embodiments, the bacteria in (a) are selected from the phyla Proteobacteria, Actinobacteria, and Firmicutes, In some embodiments, the bacteria reduce selenate. In some embodiments, the bacteria reduce selenite.

In some embodiments, the at least one selenium reducing bacteria is a plurality of different selenium reducing bacteria.

In some embodiments, the plurality of bacteria reduce selenate and selenite to Se°.

In some embodiments, the dissolved hydrogen is from hydrogen gas sparged into the water.

In some embodiments, the selecting is performed in a bioreactor comprising a plurality of hollow filaments, wherein the bacteria form a biofilm on an exterior surface of the hollow filaments and hydrogen gas is introduced to an interior lumen of the hollow filaments.

In particular embodiments, the filaments are comprised of polyester, including e.g., recycled polyester.

In another aspect, a method for selecting a selenium-reducing, petroleum contaminant-tolerant microorganism is provided, comprising:
  (a) growing a naturally-occurring selenium-reducing bacteria under conditions of low petroleum contamination,
  (b) iteratively increasing the amount of at least petroleum contamination while maintaining a biofilm, and
  (c) recovering the selenium-reducing bacteria that grow under conditions of petroleum contamination.

In some embodiments, selenium reduction is monitored at (b) to ensure the bacteria continue to reduce selenium species. In some embodiments, selenium reduction is monitored at (c) to ensure the bacteria continue to reduce selenium species.

In some embodiments, the bacteria in (a) are selected from the phyla Proteobacteria, Actinobacteria, and Firmicutes.

In some embodiments, the bacteria reduce selenate. In some embodiments, the bacteria reduce selenite.

In some embodiments, the naturally-occurring selenium-reducing bacteria is a plurality different selenium reducing bacteria.

In some embodiments, the bacteria reduce selenate and selenite to Se°.

In some embodiments, the dissolved hydrogen is from hydrogen gas sparged into the water.

In some embodiments, the selecting is performed in a bioreactor comprising a plurality of hollow filaments, wherein the bacteria form a film on the outside of the filaments and hydrogen gas is introduced inside the hollow filaments.

In particular embodiments, the filaments are comprised of polyester, including e.g., recycled polyester.

In another aspect, selenium-reducing, petroleum contamination-tolerant bacteria produced by the methods described herein are provided. In some embodiments, the selenium-reducing, petroleum contamination-tolerant bacteria is a mixture of different, selenium-reducing, high-salt bacteria.

In another aspect, a business method is provide, comprising:
   obtaining petroleum contaminated wastewater from a customer,
   removing selenium from the water using selenium-reducing, petroleum contamination tolerant bacteria,
   returning petroleum contaminated, selenium-depleted water to the customer for reuse, and
   charging the customer a price.

In some embodiments, the price for said removing and returning is less than the cost of untreated, essentially selenium-free water.

In some embodiments, the step of removing selenium is performed in a bioreactor comprised of hollow filaments for supporting a biofilm comprised of the bacteria.

In some embodiments, the selenium-reducing, petroleum contaminant tolerant bacteria are obtained by
   (a) growing a naturally-occurring selenium-reducing bacteria under conditions of low petroleum contamination,
   (b) iteratively increasing the amount of petroleum contamination, and
   (c) recovering the selenium-reducing bacteria that grow under conditions of petroleum contamination.

In some embodiments, removing selenium from the water is performed at a worksite.

In addition to the exemplary aspects and embodiments described above, further aspects and embodiments will become apparent by reference to the drawings and by study of the following descriptions.

DETAILED DESCRIPTION

I. Selenium in Brine Water and Refinery Wastewater

The present compositions and methods relate to the removal of selenium species from high salt/high TDS water and refinery water. The selenium species may be in any oxidation state (i.e., II-, 0, II, IV, and VI), as found in, e.g., selenium (Se°), selenite (Se[IV], $SeO_3^{2-}$), selenate (Se[VI], $SeO_4^{2-}$), and hydrogen selenide (Se[-II], $H_2Se$). As used herein, Se° and $H_2Se$ are considered "reduced" selenium species.

High-salt waters include brine and other wastewaters from reverse osmosis, microfiltration, ion-exchange, and other water treatment procedures. The molar concentration of salt in these waters may be as high as about 4.5 molar (M), which is the saturation level of NaCl in water. This corresponds to about 9% (wt/vol). Typical salt concentrations are lower, e.g., about 0.5 M to about 4 M, about 1 M to about 3.5 M, about 1.5 M to about 3 M, or even about 2 M. By comparison, the mammalian physiological salt concentration is about 0.150 M and seawater is about 0.5 M. As used herein, "high-salt waters" have a 1M or greater salt concentration, up to the saturation level of salt, "Low-salt Waters" have less than 1 M salt. Exemplary molar concentrations of salt are provided, above. In some embodiments, "salt" refers strictly to sodium chloride. In other embodiments, "salt" refers to any ionic compound dissolved in the water. Typical applications involve high levels of sodium chloride in combination with lower levels of other salts.

In addition to containing high levels of salts, brine and other wastewaters often contain elevated levels of other contaminants, which make them additionally hazardous and expensive to treat. In many cases, the concentration of contaminants in wastewater is a necessary consequence of a process, such as reverse osmosis or microfiltration processes, which remove but do not destroy water-borne contaminants. Similarly, high salt washes of ion-exchange resins necessary contain the removed contaminants. Selenium species are among the contaminants concentrated in high-salt wastewater.

Refinery waters include wastewater associate with various aspects of petroleum productions and refinement. Some contaminated water effluents from petroleum refining are "sour" process waters generated from desalting, topping, vacuum distillation, hydrodesulphurization, hydrocracking, catalytic cracking, coking, and the like. In addition to hydrogen sulfide, sour waters are often contaminated with organic sulfur compounds, hydrocarbons, ammonia, organic acids, and phenol. A sour water stripper apparatus may be used to remove hydrocarbons, hydrogen sulfide, ammonia and other compounds, before recycling the water for other processes, or disposal. Other wastewaters associated with petroleum refining are non-oily and non-sour but highly alkaline, and may contain spent caustic soda from sweetening units and bases used in other processes. Refinery water are often rich in selenium, particularly when they involve petroleum products obtained from marine shale environments.

A feature of the present compositions and methods is the use of a microorganism, capable of reducing selenium species in the presence or high salt and/or refinery contaminants. Preferably, such microorganisms reduce selenate (Se[VI]) and selenite (Se[IV]) to selenium (Se°), which precipitates and can readily be separated from water. Such selenium-reducing microorganisms may be selected from natural waters containing selenium species by providing a growth environment for the microorganism and gradually increasing the concentration of salts, hydrocarbons, or other contaminants in the environment.

Note that while some selenium-reducing organisms may inherently be capable of growth in "dirty" high TDS/salt waters, such organisms are incapable of growth and reduction of selenium in brine waters, or petroleum contaminated waters, as defined, herein. Some embodiments of the present compositions and methods expressly exclude the use of naturally occurring organisms that reduce selenium in dirty waters that contain low levels of TDS/salt and petroleum contaminants. Rather, such embodiments are based on the adaptation and selection of organisms that reduce selenium but are incapable of growth under the severe conditions described until such times as they are adapted and selected for growth and selenium reduction under these extreme conditions, e.g., using the described apparatus and procedures. Particular embodiments expressly exclude selenium reducing organisms that do not include at least one non-naturally occurring adaption to high TDS/salt or petroleum contaminant growth, such as those described, below.

Exemplary apparatus for maintaining a biofilm of microorganism are provided herein. Such apparatus allow nutrients, salts, acids, bases, etc., to be added to the water in which the microorganism are present and allow gases to be efficiently delivered to biolfilm.

II. Adaptation of Microorganisms to Environments

A. Adaptation to High-Salt Environments

Microorganisms are known to develop several mechanisms to withstand high salt conditions. For example, the haloarchaea and other bacteria (including *Salinibacter ruber*) accumulate high internal concentrations of potassium and chloride, minimizing the difference in osmolority between the inside and outside of the bacteria. This strategy is referred to as the "salt-in-cytoplasm" adaptation, Some bacteria also become dependent on chloride as a counter-ion and for other forms of metabolic regulation, Another strategy for existing in high-salt environments is the "compatible solute" adaptation, in which microorganism accumulate organic, osmotically-active molecules into their cytoplasm (rather than salt). These solutes can accumulate to high levels without affecting metabolism, while providing protection against the high osmolarity of the extracellular environment. Compatible solutes include amino acids and N-methyl-substituted amino acids (e.g., alanine, glycine, proline, α-glutamate, β-glutamate, and N-acetyl-β-lysine, and betaine), sugars and sugar derivatives (e.g, glucose, sucrose, mannosucrose, and trehalose,), polyols, and small peptides.

Halophilic bacteria also produce proteins that are rich in surface-exposed acidic (i.e., negatively charged) residues, which are believed to interact with salt ions to provide a hydration shell around the proteins. Membrane modifications include an increase in surface-exposed, negatively-charged phospholipids and development of an outer layer of sulphated glycoproteins. The genomes of several haloarchaea (e.g., *Halobacterium* sp. NRC-1 and *Haloarcula marismortui*) have been sequenced, allowing genes from halophiles to be cloned and transferred to other bacteria.

Both aerobic gram-negative bacteria (including members of the genera *Acinobacter, Alteromonas, Deleya, Flavobacterium, Halomonas, Halovibrio, Marinomonas, Pseudomonas*, and *Vibrio*) and aerobic gram-positive bacteria (including members of the genera *Bacillus, Marinococcus, Sporosarcina*, and *Salinococcus*) are found in brine, high-salt soils, and salterns. *Halobacterium lactussprofundi* and *Dunaliella* spp. are capable of growing in 4.8 M salt at near freezing temperatures. *Chromaltium, Ectothiorhodospina, Rhodospirfillum*, and *Thiocapsa* are found in brine exposed to light. Generally, *Halobacteria, Haloarculo, Halobacterium*, and *Halorubrum* are among the most common bacteria found growing in near-saturation salt conditions.

B. Adaptation to Petroleum Product-Contaminated Environments

Hydrocarbons that are likely to be found in refinery wastewaters can be divided into four categories: (i) saturates/aliphatics, (ii) aromatics, (iii) asphaltenes, and (iv) resins. Asphaltenes include phenols, fatty acids, ketones, esters, and porphyrins, while resins include pyridines, quinolines, carbazoles, sulfoxides, and amides. Strains of *Pseudomonas citronellolis* can be isolated from different hydrocarbon contaminated sites. *Pseudomonas, Vibro*, and *Rhodococcus* species have been adapted to metabolize some of the aliphatic and light aromatic hydrocarbons present in petroleum products, and have been proposed for use in treating oil spills. Asphaltenes and resins are more resistant to microbial degredation.

Adaptation to such hydrocarbon environments is believed to occur through one of three mechanisms, namely induction or depression of enzymes, genetic changes, or selective enrichment of existing genes or products. Selective enrichment may occur may occur through gene duplication or via plasmids.

While the present compositions, systems, and methods do not require the metabolism of petroleum products, they do require microorganisms that are tolerant of petroleum-derived contaminants in wastewater. Such environments are henceforth referred to as "petroleum-contaminated environments and organisms capable of growth in such environments are referred to as petroleum-tolerant organisms. As used herein, petroleum contaminant primary include hydrocarbons but may further include salts and other solutes found in refinery wastewater.

IV. Adapting Selenium-Reducing Microorganisms to High-salt or Petroleum-Contaminated Environments Producing a selenium reducing organism capable of growth in a high-salt environment and/or a petroleum-contaminated environment can be accomplished using one of two general strategies. A first strategy is to adapt existing selenium reducing organisms to high-salt or petroleum-contaminated environments. A second approach is to adapt an organism capable of growth in a high-salt environment or a petroleum-contaminated environment to metabolize selenium. While the latter approach may produce acceptable results, the present compositions and methods are primarily designed for the former approach, i.e., adapting existing selenium reducing organisms to growth in high salt/high TDS and/or petroleum contaminated waters. While bacteria are preferred microorganism because of their rapid growth rate, genetics, and ubiquitous presence in the environment, other microorganism can also be used (e.g., fungi, protozoans, algae, etc.)

A. Selenium Reducing Microorganisms

Several phyla of bacteria are known to include members capable of reducing selenium species, including the *Proteobacteria, Actinobacteria*, and *Firmicutes*. These bacteria are heterotrophic, requiring an organic carbon source for survival. Exemplary selenium-reducing bacteria are listed in the following Table I.

While capable of selenium reduction, the above-identified bacteria are not recognized for their ability to grow in high-salt conditions or in petroleum-contaminated environments. The present compositions and methods are drawn to the adaptation of such bacteria to high-salt and petroleum-contaminated environments.

TABLE 1

Selenate and selenite-reducing bacteria

| Selenate-reducing | Selenite-reducing | |
|---|---|---|
| *Enterobacter cloacae* | *Achromobacter xylosoxidans* | *Planomicrobium okeanokoites* |
| *Planomicrobium mcmeekinii* | *Aeromonas hydrophila* | *Pseudomonas alcaligenes* |
| *Pseudomonas alcaligenes* | *Arthrobacter koreensis* | *Pseudomonas denitrificans* |
| *Pseudomonas denitrificans* | *Brevundimonas bullata* | *Pseudomonas fluorescens* |
| *Pseudomonas stutzeri* | *Brevundimonas vesicularis* | *Pseudomonas monteilii* |
| *Roseomonas genomospecies* | *Enterobacter amnigenus* | *Pseudomonas putida* |
| | *Enterobacter cloacae* | *Pseudomonas straminea* |
| | *Escherichia hermannii* | *Pseudomonas stutzeri* |
| | *Escherichia senegalensis* | *Rahnella aquatilis* |
| | *Klebsiella pneumoniae* | *Rhodobacter sphaeroides* |
| | *Kluyvera georgiana* | *Roseomonas genomospecies* |
| | *Paenibacillus pabuli* | *Serratia marcescens* |
| | *Planococcus maitrii* | *Shewanella putrefaciens* |
| | *Planococcus maritimus* | *Sphingomonas echinoides* |
| | *Planococcus psychrotoleratus* | *Staphylococcus succinus* |
| | *Planomicrobium mcmeekinii* | *Stenotrophomonas maltophilia* |

Figure 1:
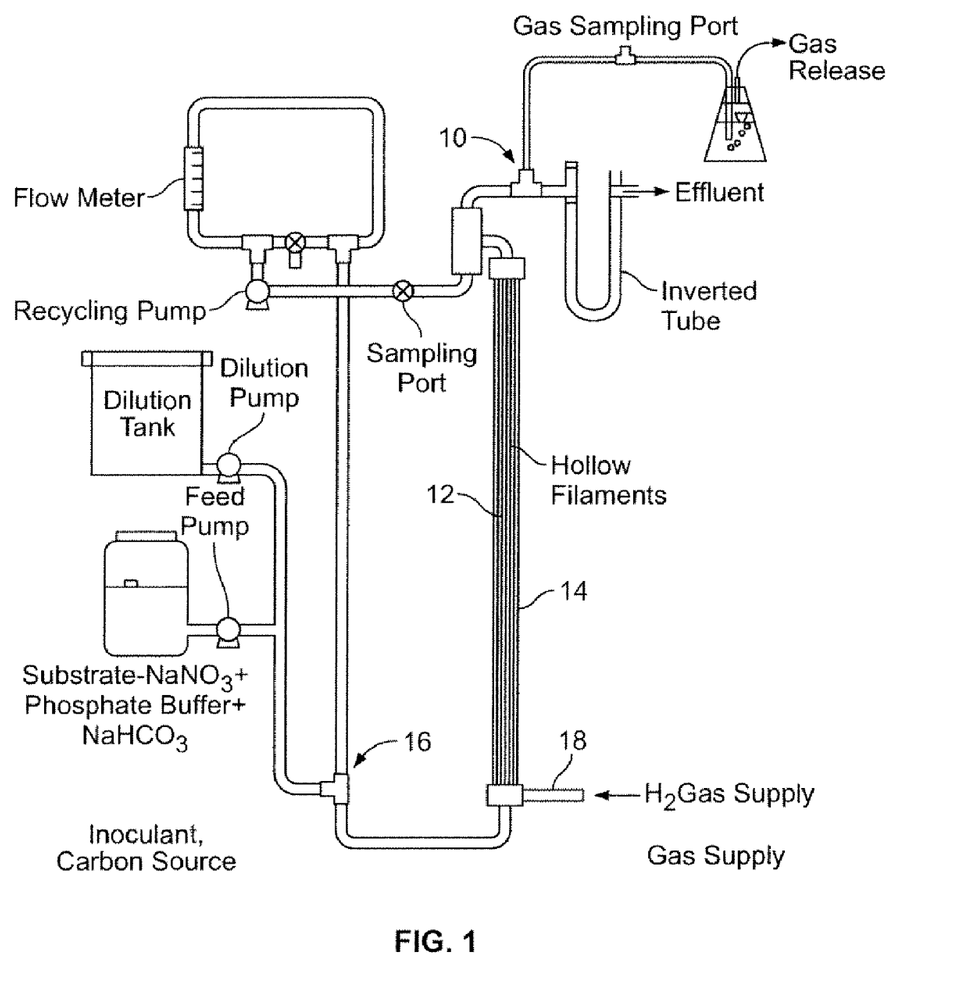
FIG. 1 illustrates a bioreactor for use in removing selenium species from water and for selecting selenium-reducing microorganism for use in different environments.

B. Apparatus for Growing and Adapting Bacteria to a High-Salt/TDS or Petroleum-Contaminated Environment and Performing Selenium Removal from Brine Waters In one method of adapting selenium reducing bacteria to a high-salt and/or petroleum-contaminated environment, selenium reducing bacteria are first grown in a bioreactor as a biofilm. The selenium reducing bacteria may be from natural waters or may be introduced from an inoculum. Exemplary selenium reducing bacteria are identified, herein. An exemplary bioreactor is shown in FIG. 1. The bioreactor features a plurality of hollow filaments comprised of a polymer (e.g., polyester, polyethylene, polypropylene, etc.). The hollow filaments have an exterior surface upon which a biofilm is formed, and an interior surface defining a lumen. Numerous other materials can be used. Gas introduced into the lumen of the hollow filaments diffuses through the wall of the filaments, becoming available to a biofilm growing on the exterior surface.

The extent of biofilm loss due to abrasion and "washing away" is much less in the exemplary hollow-fiber biofilm reactor compared to a conventional fluidized-bed bioreactor, improves biofilm accumulation and stability. This is especially important when stressing the biofilm to select for organisms that can survive under adverse growth conditions, such as the presence of high salt/TDS and/or petroleum contaminants. Moreover, since the biofilm is on the surface of the hollow filaments, the gas is applied (i.e., fluxed) directly to the biofilm through the filaments, rather than diffusing into the biofilm from the water being treated. This makes it possible to attain nearly 100% utilization of fluxed gas. The apparatus can also safely handle explosive gases, such as hydrogen, which is required for selenium reduction. U.S. Pat. No. 6,387,262 describes an apparatus suitable for use as described, and the relevant portions of the disclosure related to the apparatus are incorporated by reference, herein.

The bioreactor system 10 exemplified in FIG. 1 comprises a plurality of hollow filaments 12 housed in a tube enclosure 14. Water to be treated is supplied to the tube/inlet port 14 connected to a pipe network 16. A controllable amount of gas is sparged/fluxed into the tube 14 via gas inlet 18. A dilution and feed pump control the addition of nutrients or substrates (e.g., a carbon source) and/or an inoculum of a microorganism. Sampling ports and gas release ports are provided as needed. The water entering the tube 14 and contacting the plurality of hollow filaments 12 may be filtered or pretreated using any number of water treatment methods. The direction of flow through the filaments 12 is not critical; although it may be desirable to pumps water upward through the filaments to avoid pumping water against the flow of evolving gas. The apparatus may also include one or more side streams for premixing gas, peroxide, substrates, nutrients, inoculum, etc. in a volume of water prior to introducing such reagent into the bioreactor.

Figure 2A:
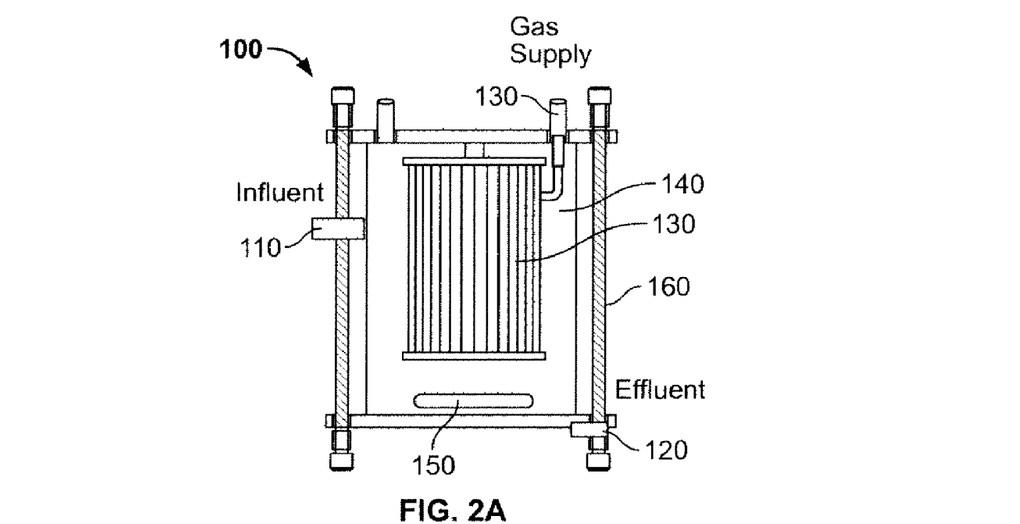
FIG. 2A shows a schematic of an exemplary bioreactor containing hollow filaments.

FIG. 2A illustrates an embodiment of a bioreactor 100 including a module of hollow filaments 130 contained within a tube/vessel 160, which defines a chamber 140 for containing water to be treated. The vessel includes an influent port 110 for receiving water to be treated, an effluent port 120 for releasing treated water, and a gas supply port 130 for supplying gas to the hollow filaments.

Figure 2B:
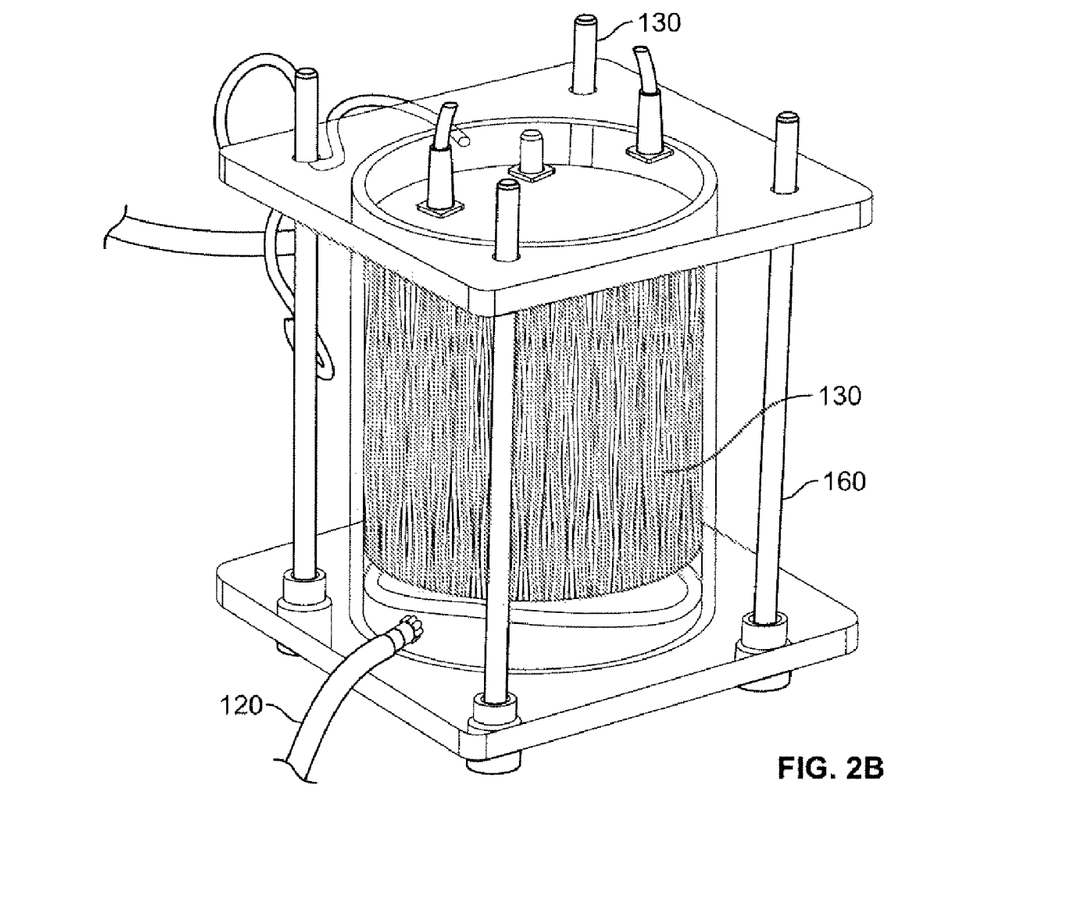
FIG. 2B is a photograph showing a prototype bioreactor.

The bioreactor may include stirring means, as exemplified by the stir bar 150 on the bottom of the bioreactor chamber 140. A photograph of a prototype apparatus is shown in FIG. 2B. The hollow filaments 130, tube/vessel 160, effluent port 120, and gas supply port 130 are indicated. Such a bioreactor may be referred to as a membrane biofilm reactor (MBfR).

Gas is directed inside the plurality of filaments, which may be potted together at one or both ends. In some embodiments, the bottom ends of the filaments are potted but open to permit the introduction of gas into the hollow filaments. The opposite end of the filaments may be potted or non-potted, allowing the fibers to move independently. The opposite end of the filaments may be sealed to prevent the escape of gas or open to allow excess gas to flow through. In related embodiment, the top of the filaments are potted but open to permit the introduction of gas into the hollow filaments, and the opposite ends are as above.

In some embodiments of the bioreactor, the tube 14 comprises a plurality of hollow filaments arranged into groups, or modules. A tube may comprise a plurality of such modules. For most embodiments, the lengths of the hollow filaments are not critical to the function of the bioreactor. However, since the total surface area of the plurality of filaments is proportional to the amount of biomass that can be supported, and ultimately the amount of contaminated water that can be treated, long filaments are preferred for high throughput applications. Such filaments may be several centimeters to several meters in length, depending on design constraints, such as the depth of a reservoir or pond, the length of tube for containing the filaments, the type of gas, the type of oxidized contaminants, the levels of oxidized contaminants, the temperature, and the pH of the water.

The filaments may be provided in a tow of hollow filaments, for example, fine filaments having an outside diameter (OD) of 100 µm or less. The tow of filaments may be potted in a module with minimal reduction in the effective surface area. Modules may be made directly from the tows without first making a fabric. The tows may also be made into open fabrics to facilitate potting, while leaving significant portions of the filaments as tows. Organization of filaments into tows is described, e.g., in U.S. Pat. No. 7,175,763.

In some embodiments, a single header module may be inserted in a reactor in a vertical configuration with the header at the bottom and the hollow filaments floating upwards. In other embodiments, a single header module may be inserted in a reactor in a vertical configuration with the header at the top and the hollow filaments oriented downward. Modules may be aerated from outside the module to remove accumulations of debris and solids. A gas stream can be fed into the lumen of the module, with the dissolved gas being used by the biofilm growing on the surface of the fiber. Hydrogen-depleted gas can be discharged with or without incineration.

In other embodiments, modules may be made of nonporous or dense walled hollow filament membranes, to provide a large surface area while avoiding the tendency of porous fibers to wet over time, which results in a drop in oxygen transfer rates. Use of small-diameter filaments helps reduce module cost and produces modules with a very large surface, The filaments have an outside diameter of 500 µm or less, or even 100 µm or less. Examples of such modules are described in U.S. Pat. No. 7,169,295.

In other embodiments, modules are made from woven, knitted, stitched or other types of fabrics containing a large number of hollow filaments. The fabric may be made with the hollow filaments and inert fibers to minimize damage to the hollow filaments during weaving. Filaments having a diameter of 20 µm or less, or even 10 µm or less, may be used. The fabric imputes strength to the fine filaments to permit biofilm growth on with minimal filament breakage. Modules may be made from fabric sheets with very high packing density to permit good substrate velocities across the surface without the need to recirculate the water being treated. Examples of such modules are described in U.S. Pat. No. 7,169,295.

In other embodiments, modules are made of hollow fibers that are melt-spun to have a partially dense, asymmetric, variable porosity, or homogenous wall that does not permit water flow but has gas permeability. Increased permeability results from thermal or physical treatment of the filaments after leaving the spinneret. Examples of this method are described in U.S. Pub. No. 2006-0037896.

In other embodiments, hollow filaments are arranged in a parallel orientation in a sheet or plate having a bottom surface and a top surface. The filament ends at the bottom end are typically open, and the open ends may be potted. Gasses are introduced into the hollow filaments via the potted bottom surface. The filament ends at the top surface may open or closed, Examples of such sheets or plates can be found, e.g. in U.S. Pat. No. 7,140,495.

As noted above, an exemplary material for use in making hollow filaments is polyester. Esters are a class of organic compounds traditionally formed by the condensation of an alcohol and an organic acid. Where the acid is a carboxylic acid, the resulting ester has the structure $R_1$—C(=O)O$R_2$, where $R_1$ and $R_2$ are independently H or myriad functional groups. Esters can also be formed from phosphoric, sulfuric, nitric, boric, benzoic, and other acids. Cyclic esters are known as lactones.

Esters participate in hydrogen bonding as hydrogen-bond acceptors. However, esters do not function as hydrogen donors. This allows esters groups to form hydrogen bonds with many other functional groups, while precluding hydrogen-bonding between esters groups. Esters are generally hydrophobic, although the nature of the $R_1$ and $R_2$-groups affects the characteristics of a particular ester.

Polyester is a polymer of one or more preselected ester monomers, typically produced by azeotrope esterification, alcoholic transesterification, acylation (i.e., the HCl method), the silyl or silyl acetate method, or the ring-opening method, and variations, thereof, depending on the particular polyester. Polyester is widely used in the manufacture of consumer products, and its mechanical properties are well known.

Polyesters include but are not limited to poly(ethylene terephthalate) (PET), poly(trimethylene terephthalate) (PTT), poly(butylene terephthalate) (PBT), poly(ethylene naphthalate) (PEN), poly(cyclohexylene dimethylene terephthalate) (PCTA), polycarbonate (PC), poly(butylene naphthalate) (PBN), and poly(lactic acid) (PLA). Polyesters may be homopolymer or heteropolymers. As used herein, heteropolymers include copolymers. A common polyester copolymers is 1,4-cyclohexanedimethanol (CHDM). For example, PCTA is a copolymer of three monomers, which are terephthalic acid, isophthalic acid, and CHDM. While some industries use the terms "polyester" and "PET" almost interchangeably, the term "polyester" refers to the entire class of compounds.

Many of the advantages of polyester are most apparent when fibers are tossed or woven into tows, ropes, fabrics, etc. For example, polyester is widely used in the textile industry. The most widely used polyester is PET (or PETE), which exists in amorphous (transparent) and semi-crystalline (white or opaque) forms and is readily made into fibers and sheets. PET and another polyester of a dihydric alcohol and terephthalic acid are commonly used to make rope.

In addition to being inexpensive to produce, polyesters are particularly strong, resilient, resistant to abrasion, and resistant to stretching and shrinking. Polyester textiles are wrinkle resistant, mildew resistant, fast drying, and retain heat-set pleats and creases. Polyester displays excellent resistance to oxidizing agents, cleaning solvents, and surfactants. While resistant to sunlight, UV stabilizers are typically added for use outdoors or exposed to UV light.

Polyesters, like most thermoplastics, are recyclable and may be may be virgin polyesters, recycled polyesters, post consumer polyesters, recycled monomers, or combinations and variations, thereof. Some polyesters, including PET, offer the additional advantage of containing only carbon, oxygen, and hydrogen (i.e., no sulfur, phosphorus, nitrogen, etc.), which makes them candidates for incineration.

Exemplary polyester hollow filaments are made of melt-spinnable polyester, such as PET, that is melted and pressed through a hole of a spinneret, quenched in water or in an air stream, stretched in one or more steps in combination with heating, and then wound onto on a spool using a winding machine. The hollow filaments are fine, effectively "endless" flexible hollow polyester tubes, which can be cut to any length as needed. The filaments having an exterior surface that is typically exposed to the wastewater, and an interior surface for interacting with sparged gas. The interior surface defines a hollow interior space. The preferred diameter of polymer filaments depends on the particular embodiment. The polyester filaments may be less than 500 µm in diameter, or even less than 100 µm in diameter. The filaments, may even be less than 50 µm, less than 20 µm, or even less that 10 µm in diameter. The hollow filaments may have a uniform diameter or be heterogenous with respect to diameter. Where the filaments are of heterogenous diameter, the diameter may fall within a preselected range.

The hollow polyester filaments may be tossed into bundles to form multifilament yarns, which are then assembled into modules for use in a bioreactor, to be described. Filaments of less than 10 dtex (i.e., decitex=1 gram per 10,000 meters) are preferred for yarns, while filaments of more than 100 dtex are typically used as monofilaments. Intermediate filaments are used in either form. Both mono and multifilaments can be used as warp or weft in technical fabrics. Loose bundles of filament that are not woven into fabrics may also be used.

The diffusion of gas through a polymer membrane is generally described by Fick's laws of diffusion. The solubility coefficient depends on the particular polymer-gas combination and Henry's law. The permeation of low molecular weight gases in rubbery polymers (below their glass transition temperatures) at moderate pressures is Fickian and follows Henry's law for different sorption modes (i.e. absorption, the adsorption, plus trapping in microvoids, clustering, and aggregation). Klopffer, M. H. and Flaconnèche, B., Oil & Gas Science and Technology—Rev. IFP, 56, 2001, No. 3).

The burst pressure of a hollow polyester filament can be calculated using the formula:

$$P = T \cdot (OD^2 - ID^2)/(OD^2 + ID^2)$$

where P is burst pressure, T is tenacity, and OD and ID are outside and inside diameter, respectively. OD and ID are preselected variables and tenacity is a constant associate with a particular polymer.

For example, a PET filament having and OD of 200 μm, an ID of 100 μm, and a tenacity of approximately 30 cN/tex (i.e., 400 MPa) has a burst pressure of 240 MPa. A working pressure of about 1% of the burst pressure is, therefore, 2.4 MPa, or 337 PSI. In one embodiment, an apparatus comprised of a plurality of filaments is provided, where the filaments have a burst pressure P, and the apparatus is operated at a pressure of less than about 10% of the burst pressure, more preferably at less than about 5% of the burst pressure, and still more preferably at less than about 2% of the burst pressure Preferred filament diameters for use as described are from about 0.05 mm to about 5 mm (OD), or even from about 0.10 mm to about 3 mm. The optimal shape of hollow filaments is round, although irregular shaper are expected to produce satisfactory results. Consistent density is preferred but not required. Preferred tenacity values are from about 10 to about 80 cN/tex, or even from about 20 to about 60 cN/tex.

Percent void volume (% V) may be calculated using the formula:

$$\% V = T \cdot (\text{inside area})/(\text{outside area}) \times 100$$

An acceptable range for void volume is from about 1% to about 99%, while a preferred range for some embodiments is from about 25% to about 50%.

The use of polyester hollow filaments offers several advantages over other polymers and materials, some of which are described, below.

First, the extent of biofilm loss due to abrasion and "washing away" is much less in the hollow-fiber biofilm reactor (herein "bioreactor") than in the fluidized-bed bioreactor. The ester groups of polyester are cable of forming interactions with bacterial improving biofilm accumulation and stability.

Second, since the biofilm is on the surface of the hollow filaments, the hydrogen flux is applied directly into the biofilm, rather than diffusing into the biofilm from the water being treated. This makes it possible to attain nearly 100% utilization of fluxed $H_2$ (and/or $O_2$ or other gases, depending on the embodiment), which makes the reaction process more economical. U.S. Pat. No. 6,387,262 describes an apparatus for safely handling $H_2$ with minimal risk of explosion. Polyester is permeable to $H_2$ and $O_2$, allowing ready diffusion of gases into the biofilm.

Third, the use of polyesters allows bioreactors to be produced in essentially any number, from recycled or partially-recycled polyester, with reduced impact to the environment in terms in of e.g., petroleum distillates, new monomer synthesis, reagents and energy for esterification or other synthesis methods, etc. Using an abundant recycled "plastic" material for the manufacture of hollow filaments for bioreactors is an efficient and environmentally-friendly strategy for water treatment.

Fourth, the hollow polyester filaments can be incinerated if they become unsuitable for use, e.g., due to contamination by an undesirable bacterium or other organism. While the hollow polyester filaments can also be disinfected with ozone, peroxide, bleach, etc., it may in some cases be advantageous to incinerate the hollow polyester filaments. Because polyester contains only carbon, hydrogen and oxygen, and does not contain e.g., sulfur and nitrogen, polyester can be incinerated and/or used as fuel, without the production of e.g., toxic sulfur and nitrogen compounds. The use of adhesives, sealants, and related materials low in sulfur and nitrogen for potting the hollow polyester filaments further reduces the amount of toxic waste products produced by incineration.

The lengths of the hollow polyester filaments is generally not critical to the function of the bioreactor. However, since the total surface area of the plurality of filaments is proportional to the amount of biomass that can be supported, and ultimately the amount of contaminated water that can be treated, long filaments are preferred for high throughput applications. Such filaments may be several centimeters to several meters in length, depending on design constraints, such as the depth of a reservoir or pond, the length of tube for containing the filaments (if present), the type of gas, the type of oxidized contaminants, the levels of oxidized contaminants, the temperature, and the pH of the water.

In some embodiments, the polyester hollow filaments are provided in a tow of hollow filaments, for example, fine filaments having an outside diameter (OD) of 100 μm or less. The tow of filaments may be potted with minimal reduction in effective surface area. The tows may also be made into open fabrics to facilitate potting, while leaving significant portions of the filaments as tows. Organization of filaments into tows is described e.g., in U.S. Pat. No. 7,175,763.

In some embodiments a header directs gas to one (or more often a plurality) of filaments in a reactor in a vertical configuration with the header at the bottom and the hollow filaments floating upwards. In some embodiments, the header is at the top and the hollow filaments oriented downward. In other embodiments, the hollow filaments are oriented outward from the header in the form of a coil, loop, grid, etc. The hollow polyester filaments may be, e.g., at least 50, at least 100, at least 300, at least 500, at least 700, at least 1,000, at least 1,500, and even at least 2,000 μm. Heavier filaments are well suited for coils and loops.

In other embodiments, modules are made from woven, knitted, stitched or other types of fabrics containing a large number of hollow filaments The fabric may be made with the hollow filaments and inert fibers to minimize damage to the hollow filaments during weaving. Filaments having a diameter of 20 μm or less, or even 10 μm or less, may be used. The fabric imputes strength to the fine filaments to permit biofilm growth on with minimal filament breakage. Modules may be made from fabric sheets with very high packing density to permit good substrate velocities across the surface without the need to recirculate the water being treated. Examples of such modules are described in U.S. Pat. No. 7,169,295.

In some embodiments, hollow fibers that are melt-spun to have a partially dense, asymmetric, variable porosity, or homogenous wall that does not permit water flow but has gas permeability, Increased permeability results from thermal or physical treatment of the filaments after leaving the spinneret. Examples of this method are described in U.S. Pub. No. 2006-0037896.

In other embodiments, hollow polyester filaments are arranged in a parallel orientation in a sheet or plate having a bottom surface and a top surface. The filament ends at the bottom end are typically open, and the open ends may be Potted. Gasses are introduced into the hollow filaments via the potted bottom surface. The filament ends at the top surface may open or closed. Examples of such sheets or plates can be found, e.g., in U.S. Pat. No. 7,140,495.

Where the filaments are closed at the end distal to the gas inlet end, the ends may be closed by the thermal sealing (i.e., pinching and melting), using sealant or adhesive, or in the potting process.

C. Selection of Selenium Reducing Bacteria Tolerant to High Salt/TDS

For the adaptation of selenium-reducing bacteria to high-salt conditions, selenium reducing bacteria are first grown under low salt conditions in the presence of selenium and an organic carbon source. The carbon source may include sugars or complex carbohydrates, animal or plant renderings, acetate, etc. While the carbon source for selenium-reducing bacteria is not critical, the selection of high-salt-tolerant bacteria may be assisted by the selection of a readily metabolized carbon source, such as glucose, This avoids stressing the bacteria, which encounter an increasingly hostile environment during the selection process.

Hydrogen gas is sparged through the bioreactor to allow the bacteria to reduce selenium species. Use of the above-described apparatus ensures nearly 100% hydrogen dissolution in the water. Reduction is monitored to ensure that the bacteria in the reactor retain the ability to reduce selenium species.

Using such methods, a biofilm of selenium reducing bacteria is allowed to form in a bioreactor with selenium-reducing activity being monitored periodically. Methods for measuring the levels of selenium species are known in the art and several methods are described in Example 1. In some embodiments, endogenous bacteria present in the water sample serve as the initial inoculum. In other embodiments, an inoculum of one or more of the above-identified selenium reducing bacteria (e.g., Table 1) is introduced into the bioreactor to seed the biofilm.

Once a biofilm has formed and is confirmed to reduce selenium species, increasing amounts of salt are added to the water in the reactor to select for bacteria capable of growing under high conditions. The rate of increase of the salt concentration is selected to maintain a portion of the biofilm in the reactor, while non-salt-tolerant bacteria are washed away. Selenium reduction is monitored to ensure the bacteria in the biofilm retain the ability to reduce selenium compounds. The salt concentration is gradually and iteratively increased by, e.g., in about 0.1, about 0.2, about 0.3, about 0.4, or even about 0.5 M increments, until a desired sat concentration is achieved. Preferred selenium reducing bacteria can grow in at least 1 M, at least 2 M, at least 3 M, and even at least 4 M salt. While the salt is generally sodium chloride, minor amounts of other salts, including but not limited to lithium, potassium, magnesium, calcium, calcium, fluoride, chloride, bromide, sulfate, sulfite, nitrate, nitrite, and iodide salts, may also be present.

The bacteria in the biofilm may be a single species, or preferably, a plurality of species that can perform different selenium reduction steps. Pure or mixed cultures of these selenium reducing, high-salt tolerant bacteria are then used to prepare glycerol stocks, plates, frozen stocks, etc., which may be used to inoculate further bioreactors. Pure or mixed cultures can be harvested from the bioreactor at any time during selection, and used to reduce selenium in water containing salt/TDS at or below the concentration at which the bacteria were selected. Thus, different pure or mixed cultures may be selected for use in e.g., 0.5-1 M salt, 1-1.5 M salt, 1.5-2 M salt, 2.5-3 M salt, 3.5-4 M salt, etc.

In this manner, a selenium reducing high salt/TDS-tolerant organism can be introduced into bioreactor to in the field to affect selenium reduction. A plurality of different bacteria may be used, for example, different, isolates, species, genera, phyla, etc. Each bacteria may perform a different selenium reduction. Mixtures of different bacteria may be provided in a mixed culture or maintained separately until inoculation into a bioreactor.

D. Selection of Selenium Reducing Bacteria Tolerant to Petroleum Contaminants

Selenium reducing bacteria are first grown under low petroleum contaminant conditions in the presence of selenium and an organic carbon source. The carbon source may include sugars or complex carbohydrates, animal or plant renderings, acetate, etc. As noted above, the carbon source for selenium-reducing bacteria is not critical; however, the selection of petroleum-contaminant tolerant bacteria may be assisted by the selection of a readily metabolized carbon source, such as glucose, to reduce stress on the bacteria.

Hydrogen gas is sparged through the bioreactor to allow the bacteria to reduce selenium species, and selenium reduction is monitored (as above) to ensure that the bacteria in the reactor retain the ability to reduce selenium species. In some embodiments, endogenous bacteria present in the water sample serve as the initial inoculum. In other embodiments, an inoculum of one or more of the above-identified selenium reducing bacteria (e.g., Table 1) is introduced into the bioreactor to seed the biofilm. *Pseudomonas, Vibrio*, and *Rhodococcus* species are known to metabolize petroleum products and several *Pseudomonas* species are known to reduce selenium species. Therefore, *Pseudomonas* species are ideal candidates for adaptation to petroleum-contaminated environments.

Once a biofilm has formed and is confirmed to reduce selenium species, increasing amounts of petroleum contaminants are added to the water in the reactor to select for bacteria capable of growing under such conditions. The rate of increase of petroleum contaminants is selected to maintain a portion of the biofilm in the reactor, while non-petroleum contaminant-tolerant bacteria are washed away. Selenium reduction is monitored to ensure the bacteria in the biofilm retain the ability to reduce selenium compounds. The concentration of petroleum products is gradually and iteratively increased until refinery wastewater conditions are achieved.

Refinery wastewater may be assumed to be at or near saturation with respect to various different petroleum products, some of which may be known and others of which may not be known. Common aromatic contaminants include benzene, toluene, 1-ethyl benzene, 3-methyl-benzene, tri-methyl-benzene, o-xylene, m-xylene, p-xylene, and naphthalene. Other contaminants include acetone, ethyl acetate, ethyl ether, methyl isobutyl ketone, n-butyl alcohol, cyclohexanone, methanol, methyl ethyl ketone, isobutanol, pyridine, kerosene, and 2-ethoxyethanol. Refinery wastewaters may also include such metal contaminants as arsenic, barium, beryllium, cadmium, chromium, cobalt, copper, iron, lead, manganese, mercury, molybdenum, nickel, silicon, silver, and vanadium.

Petroleum products are often described in terms of there "PIONA" profile, wherein P=Paraffins (n-paraffins, n-alkanes), I=Isoparaffins (branched alkanes), O=Olefines (alkenes, paraffins with one or several double bonds), N=Naphthenes (saturated ring compounds, usually with alkyl substituents), and A=Aromatics (simple aromatics and alkyl substituted aromatics). In whole crude oil, each of these components accounts for about 20% of the volume.

One way to adapt microorganisms to refinery wastewater without knowing the identity or concentrations or all the petroleum contaminants is to add increasing amounts of refinery water to a bioreactor, e.g., 1%, 2%, 3%, 4%, 6%, 8%, etc. until the microorganisms are able to grow in undiluted refinery water (100%). It is expected that different refinery wastewaters will contain different levels of contaminants; although most refinery wastewaters are likely to be similar in content.

The bacteria in the biofilm may be a single species, or preferably, a plurality of species that can perform different selenium reduction steps. Pure or mixed cultures of these selenium reducing, petroleum contaminant-tolerant bacteria are then used to prepare glycerol stocks, plates, frozen stocks, etc., which may be used to inoculate further bioreactors. Pure or mixed cultures can be harvested from the bioreactor at any time during selection.

In this manner, a selenium reducing petroleum contaminant-tolerant organism can be introduced into bioreactor to in the field to affect selenium reduction in petroleum-contaminated wastewater.

E. Selection of Selenium Reducing Bacteria Tolerant to Mixed Contaminants

While the adaptation of selenium reducing bacteria to high salt/TDS waters and petroleum-contaminated waters is described separately, one skilled in the art will recognize that such adaptation can be combined, For example, bacteria may be adapted to a high salt environment that also contains petroleum contaminants or refinery wastewater that also contains high salt. The latter category includes refinery brine water.

For such adaptation, microorganism may first be adapted to a petroleum contaminated environment or first adapted to a high salt environment, and then adapted to the other environment. Alternative, the bacteria may be adapted simultaneously, e.g., by gradually increasing the levels of both salt and petroleum contaminant.

IV. Selenium Removal Kits and Systems

Selenium-reducing, high salt/TDS-tolerant microorganisms, and/or petroleum contaminant-tolerant organisms can be provided as frozen stocks, on plates, or in culture for inoculating bioreactors. In some embodiments, the bacteria are provided in combination with a bioreactor or bioreactor system, e.g., in the form of a selenium removal kit, package, or system. Such kits typically comprise a bioreactor, one of more bacterial inocula, and, optionally, assay kits for measuring the levels of selenium species in water.

The selenium kits may be stand-alone water treatment apparatus or may be designed for installation in an existing water treatment system.

V. Business Methods

A feature of the present compositions and methods is the removal or selenium from brine and other high salt waters and/or from refinery wastewaters. Such waters represent a significant problem for argriculture and industry in terms of disposal cost and replacement. Depending on the size of the operation, brine and refinery water may account for many thousands of gallons of water that cannot be further reused because of the high-salt/TDS and/or petroleum contaminants, and which must be treated prior to disposal.

In addition to the obvious cost or replacing brine and/or refinery water, the pricing structure of water in some water management districts amplifies these costs and makes wastewater management even more critical. For example, many municipal water districts (i.e., operated by state and local governments) utilize a tiered water pricing structure, which allows a user to purchase relatively low quality water for a reduced price, but only up to a preset amount (i.e., volume). Once this amount is exceed, a user must switch to the next higher tier water (in terms of quality and price), even if the lower quality, less expensive water, is suitable for the application. Water that becomes brine and other high salt water, or becomes contaminated with petroleum products, is lost for further use, often requiring the purchase of more expensive, higher tier water for the subsequent use.

The ability to remove accumulated selenium from high salt/TDS wastewater, in particular, allows such water to be further recovered by desalination (e.g., evaporation and other well-known methods) and reused for a variety of agricultural and industrial purposes. One common method of desalination is simply to "pond" the water, and then collect the evaporated liquid. This avoids the need to purchase additional, often more expensive water from the municipal water district. In other embodiments, the high-salt, selenium-depleted water is reused for regenerating ion-exchange media or other applications where high-salt is tolerated but high selenium levels are unacceptable. Exemplary uses for selenium-depleted brine water are in the chloralkali process to make sodium hydroxide, chlorine, hydrogen, hypochlorite, and chlorate salts, and in the Solvay process to produce sodium carbonate. Selenium depleted petroleum-contaminated water can be further processed to remove the petroleum products, or used for further refinery processes.

The present compositions and methods can, therefore, be used to recover brine and other high salt/TDS water, and/or petroleum contaminated water, thereby saving the customers/consumers of municipal water supplies money and extending the use of scarce resources.

In one business method based on the present compositions, systems, and methods, high-salt wastewater is treated in a bioreactor with selenium-reducing, high-salt tolerant bacteria, and the owner of the water is charged an amount per unit volume of treated water. This amount will preferably be less than cost of replacement water. This business model contemplates the use of a portable bioreactor system that can be taken to a worksite, as well as the use of fixed location bioreactor system.

In another business method, high-salt wastewater is treated in a bioreactor with selenium-reducing, high-salt tolerant bacteria, and the owner of the water is charged an amount per unit amount of selenium removed. As above, this business model contemplates the use of a portable bioreactor system that can be taken to a worksite, as well as the use of fixed location bioreactor system.

In yet another business methods a high-salt wastewater bioreactor and selenium-reducing, high-salt tolerant bacteria, are sold to owners of selenium-contaminated brine waters, preferably as a cost that is less than that required to replace the contaminated water. This business model contemplates that the end-user of the system will buy, build, and/or maintain (optionally with product support) a bioreactor system at the worksite.

In another business method based on the present compositions, systems, and methods, petroleum-contaminated wastewater is treated in a bioreactor with selenium-reducing, petroleum contaminant-tolerant bacteria, and the owner of the water is charged an amount per unit volume of treated water. This amount will preferably be less than cost of replacement water. This business model contemplates the use of a portable bioreactor system that can be taken to a worksite, as well as the use of fixed location bioreactor system.

In yet another business method, selenium and petroleum-contaminated wastewater is treated in a bioreactor with selenium-reducing, petroleum contaminant-tolerant bacteria, and the owner of the water is charged an amount per unit amount of selenium removed. As above, this business model contemplates the use of a portable bioreactor system that can be taken to a worksite, as well as the use of fixed location bioreactor system.

In yet another business method, a bioreactor and selenium-reducing, petroleum-contaminant-tolerant bacteria, are sold to owners of selenium-contaminated refinery water, preferably at a cost that is less than that required to replace the contaminated water. This business model contemplates that the end-user of the system will buy, build, and/or maintain (optionally with product support) a bioreactor system at the worksite.

In all cases, the business methods are based on the value of recovered water, which would normally be lost due to the present of contaminants such as selenium.

These and other applications and implementations will be apparent to artisans, While various embodiments of the present invention have been shown and described, it should be understood that other combinations, modifications, substitutions and alternatives will be apparent to one of ordinary skill in the art. Such combinations, modifications, substitutions, and alternatives can be made without departing from the spirit and scope of the invention, which should be determined from the appended claims.

EXAMPLES

Example 1

Methods for Measuring the Levels of Selenium Species

Methods for measuring the levels of selenium species are known in the art. For example, selenite can be measured by flame atomic absorption or hydride generation atomic absorption spectrometry (i.e., HGAAS analysis), described by Zhang et al. ((1999) *Sci. Total Environ.* 229:183-93; (1999) *Environ. Sci. Technol.* 33:1652-56). Total soluble selenium can be measures by oxidizing all species to Se(VI) with $K_2S_2O_8$, then reducing all species to Se[IV] with 6 M HCl, and then applying HGAAS analysis. Total selenium levels can be determined by reducing all selenium species to Se°, e.g., with ascorbic acid, and measuring the amount of metal-loid produced. Se[II-] levels are calculated as the difference between Se(IV) levels in a sample treated with $K_2S_2O_8$ in the presence and absence of $Mn^{2+}$. The In this manner, the levels of each selenium species in water can be determined (reviewed in Siddique, T. et al. (2005) *J. Environ. Qual.* 34:217-26).

Atomic absorption spectroscopy (generally, "AA") can also be used following the reduction of all selenium species using zinc/hydrochloric acid or sodium tetrahydroborate. Various modifications have been described to increase detection sensitivity and selectivity (reviewed in, e.g., Campbell, A. D, (1984) *Pure & Appl. Chem.* 56:645-51).

Selenium can also be detected using molecular fluorescence, in which Se[IV] reacts with aromatic 1,2-diamines in acid to form piazselenols, which can be detected fluorometrically in non-polar solvents. The use of 3,3'-diaminobenzidine, 4,5-benzopiazselenol, 2-3-diaminonaphthalene, and other compounds have been described (Campbell, A. D. (1984) *Pure & Appl. Chem.* 56:645-51). Gas-liquid (GLC) chromatography, nuclear/neutron activation analysis (NAA), and X-ray fluorescence analysis (XFA) have also bee used to detect selenium species (reviewed in Ben, E. M. (1981) *Environ. Health Persp.* 37:183-200). A more recent method for selenium detection is low injection-capillary electrophoresis system with contactless conductivity detection, as described in (Kubáň, P. (2004) *Analytical and Bioanalytical Chemistry* 378:378-82.

Selenium can also be detected using ion chromatography (IC), as described, e.g., in Emteborg, H. et al. (1998) *Analyst* 123:893-98 and Sarzanini, C. and Bruzzoniti, M. C. (2001) *TrAC Trends in Analytical Chemistry* 20:304-10).

Example 2

Selection of Selenium Reducing Microorganisms

MBfR reactors as described, herein, are assembled and operated for nitrate or perchlorate reduction using endogenous organisms as is generally known in the art. Reactors using polyester filaments may be used in view of the aforementioned advantages of this particular polymer. During initial operation, reactors are fed influent "natural" wastewater or "synthetic" or "defined" influent waste water, consisting of substantially uncontaminated water into which known amounts of TDS, nitrate, or nitrite are added. In either case, selenium is present in a known amount.

Effluent water can be analyzed for selenate reduction as described in Example 1. Notably, the detection limit for selenate is about 6 ppb by IC and 4 ppb for AA. Using IC, the partially reduced product, selenite, elutes with carbonate, which peak is readily distinguishable from the selenate peak. A more dramatic indication of successful selenate (and selenite) reduction is the appearance of a red-colored precipitate on surfaces of the MBfR apparatus, which represents Se° (i.e., Se(s)). In some cases, it may be desirable to raise the pH of the influent water slightly to maintain a pH of $\geq 7.5$, to reduce the precipitation of Se° in the reactor and associated plumbing, and then lower the pH of the effluent water to produce the red precipitate characteristic of successful selenium reduction. Generally, initial selenate (or selenite) reduction under low TDS/salt concentrations can be mediated by endogenous organisms present in the contaminated water. Alternatively, a selenium reducing organism as described, herein, is added to the water.

Once selenium reduction is established, the TDS/salt concentration in the water is gradually increased. This can be accomplished by gradually and consistently increasing the TDS/salt concentration of the influent water over time, by periodically spiking the influent water with high TDS/salt concentrations, or combinations, thereof, such as spiking followed by a continued elevation of increased TDS/salt. The target TDS/salt concentration is at least about 10 g/d, and preferably about 15 g/d, 20 g/d, 25 g/d, or even 30 g/d, or higher. In some cases, the final target conditions resemble those of brine water.

The reduction of selenium is continuously or periodically monitored. Selenium reduction is expected to initially decrease with increasing TDS/salt concentration; however, reduction is then expected to slowly increase (i.e. resume) as the organisms become acclimated to the higher TDS/salt concentrations, Where a dramatic decrease in selenium reduction occurs, the elevated TDS/salt concentrations should be maintained (or slightly lowered) until selenium reduction begins to increase.

Using the described apparatus and methods a selenate removal flux of between about 40-100 mg Se $m^{-2}d^{-1}$ or even 150 mg Se $m^{-2}d^{-1}$ or higher is expected using $H_2$ as the sole electron donor at a pressure of about 15-30 psig.

What is claimed is:

1. A method for removing selenium species from high-salt waters, comprising:
   contacting high-salt water having a sodium chloride concentration of 1 M or greater, with at least one selenium-reducing bacteria capable of growing in said high-salt water, in the presence of dissolved hydrogen and an organic carbon source, said contacting forming a reduced selenium species, and
   separating the high-salt water from the reduced selenium species.

2. The method of claim 1, wherein the bacteria is selected by:
   (a) growing a naturally-occurring selenium-reducing bacteria in water, in the presence of dissolved hydrogen and an organic carbon source, to form a biofilm comprising said bacteria,
   (b) iteratively increasing the sodium chloride concentration of the water to at least 1 M, while maintaining a biofilm comprised of the bacteria that grow under such conditions, and washing non-salt-tolerant bacteria away from said biofilm, and
   (c) recovering the selenium-reducing bacteria that grow under high-salt conditions of 1 M or greater sodium chloride concentration.

3. The method of claim 2, wherein the bacteria reduce selenate.

4. The method of claim 2, wherein the bacteria reduce selenite.

5. The method of claim 2, wherein the bacteria reduce selenate and selenite to Se°.

6. The method of claim 1, wherein the dissolved hydrogen is from hydrogen gas sparged into the water.

7. The method of claim 1, performed in a bioreactor comprising a plurality of hollow filaments, wherein the bacteria form a biofilm on an exterior surface of the hollow filaments and hydrogen gas is introduced to an interior lumen of the hollow filaments.

8. The method of claim 7, wherein the filaments are comprised of a polymer selected from polyester, polyethylene, and polypropylene.

9. A method for selecting a selenium-reducing, high-salt-tolerant microorganism, comprising:

(a) growing a naturally-occurring selenium-reducing bacteria in water, in the presence of dissolved hydrogen and an organic carbon source, to form a biofilm comprising said bacteria,
   (b) iteratively increasing the sodium chloride concentration of the water to at least 1 M, while maintaining a biofilm comprising bacteria that grow under such conditions, and washing non-salt-tolerant bacteria away from said biofilm, and
   (c) recovering the selenium-reducing bacteria that grow in a water having high-salt conditions of 1 M or greater sodium chloride concentration.

10. The method of claim 9, wherein the bacteria reduce selenate.

11. The method of claim 9, wherein the bacteria reduce selenite.

12. The method of claim 9, wherein the bacteria reduce selenate and selenite to Se°.

13. The method of claim 9, wherein the dissolved hydrogen is from hydrogen gas sparged into the water.

14. The method of claim 9, performed in a bioreactor comprising a plurality of hollow filaments, wherein the bacteria form a film on the outside of the filaments and hydrogen gas is introduced inside the hollow filaments.

15. The method of claim 14, wherein the filaments are comprised of a polymer selected from polyester, polyethylene, and polypropylene.

16. Selenium-reducing, high-salt-tolerant bacteria produced by the method of claim 9.

17. A business method, comprising:
   obtaining high-salt wastewater from a customer, said high-salt wastewater having a sodium chloride concentration of 1 M or greater,
   removing selenium from the wastewater by contacting said wastewater with selenium-reducing, high-salt tolerant bacteria, in the presence of dissolved hydrogen and an organic carbon source, said contacting forming a reduced selenium species,
   separating high-salt water from the reduced selenium species,
   returning high-salt, selenium-depleted water to the customer for reuse, and
   charging the customer a price.

18. The business method of claim 17, further including desalinating the high-salt, selenium-depleted water.

19. The business method of claim 17, wherein the selenium-reducing, high-salt tolerant bacteria are obtained by
   (a) growing a naturally-occurring selenium-reducing bacteria in water, in the presence of dissolved hydrogen and an organic carbon source, to form a biofilm comprising said bacteria,
   (b) iteratively increasing the sodium chloride concentration of the water to at least 1 M, while maintaining a biofilm comprising bacteria capable of growing under such conditions, and washing non-salt-tolerant bacteria away from said biofilm, and
   (c) recovering the selenium-reducing bacteria that grow under high-salt conditions of 1 M or greater sodium chloride concentration.

20. A method for removing selenium species from petroleum-contaminated water, comprising
   contacting petroleum-contaminated water with at least one selenium-reducing bacteria capable of growing in petroleum-contaminated water, in the presence of dissolved hydrogen and an organic carbon source, said contacting forming a reduced selenium species, and
   separating the water from the reduced selenium species wherein the bacteria is selected by:
(a) growing a naturally-occurring selenium-reducing bacteria in water, in the presence of dissolved hydrogen and an organic carbon source, to form a biofilm comprising said bacteria,
(b) iteratively increasing the amount of at least one petroleum contaminant in the water, while maintaining a biofilm comprising bacteria that grow under such conditions of petroleum contamination, and washing non-petroleum-tolerant bacteria away from said biofilm, and
(c) recovering the selenium-reducing bacteria that grow under such conditions of petroleum contamination.

21. A method for selecting a selenium-reducing, petroleum contaminant-tolerant microorganism, comprising:
(a) growing a naturally-occurring selenium-reducing bacteria in water, in the presence of dissolved hydrogen and an organic carbon source, to form a biofilm comprising said bacteria,
(b) iteratively increasing the amount of at least one petroleum contaminant in the water, while maintaining a biofilm comprising bacteria that grow under such conditions of petroleum contamination, and washing non-petroleum-tolerant bacteria away from said biofilm, and
(c) recovering the selenium-reducing bacteria that grow under such conditions of petroleum contamination.

22. The method of claim 21, wherein the bacteria reduce selenate.

23. The method of claim 21, wherein the bacteria reduce selenite.

24. The method of claim 21, wherein the bacteria reduce selenate and selenite to Se°.

25. The method of claim 21, wherein the dissolved hydrogen is from hydrogen gas sparged into the water.

26. The method of claim 21, performed in a bioreactor comprising a plurality of hollow filaments, wherein the bacteria form a film on the outside of the filaments and hydrogen gas is introduced inside the hollow filaments.

27. The method of claim 26, wherein the filaments are comprised of a polymer selected from polyester, polyethylene, and polypropylene.

28. Selenium-reducing, petroleum contamination-tolerant bacteria produced by the method of claim 21.

29. A business method, comprising:
obtaining petroleum-contaminated wastewater from a customer,
removing selenium from the wastewater using selenium-reducing, petroleum contamination tolerant bacteria,
returning petroleum-contaminated, selenium-depleted water to the customer for reuse, and
charging the customer a price;
wherein the selenium-reducing, petroleum contamination tolerant bacteria are obtained by:
(a) growing a naturally-occurring selenium-reducing bacteria in water, in the presence of dissolved hydrogen and an organic carbon source, to form a biofilm comprising said bacteria,
(b) iteratively increasing the amount of at least one petroleum contaminant in the water, while maintaining a biofilm comprising bacteria that grow under such conditions of petroleum contamination, and washing non-petroleum-tolerant bacteria away from said biofilm, and
(c) recovering the selenium-reducing bacteria that grow under such conditions of petroleum contamination.

* * * * *